(12) United States Patent
Shiga et al.

(10) Patent No.: US 12,411,149 B2
(45) Date of Patent: Sep. 9, 2025

(54) SPECIMEN TRANSPORT DEVICE, SPECIMEN ANALYSIS SYSTEM, SPECIMEN PRETREATMENT SYSTEM, AND SPECIMEN TRANSPORT METHOD

(71) Applicant: HITACHI HIGH-TECH CORPORATION, Tokyo (JP)

(72) Inventors: Yuichiro Shiga, Tokyo (JP); Kuniaki Onizawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 691 days.

(21) Appl. No.: 17/785,105

(22) PCT Filed: Dec. 1, 2020

(86) PCT No.: PCT/JP2020/044721
§ 371 (c)(1),
(2) Date: Jun. 14, 2022

(87) PCT Pub. No.: WO2021/140788
PCT Pub. Date: Jul. 15, 2021

(65) Prior Publication Data
US 2023/0027956 A1    Jan. 26, 2023

(30) Foreign Application Priority Data
Jan. 8, 2020   (JP) ................................ 2020-001749

(51) Int. Cl.
*G01N 35/02*    (2006.01)
*B07C 5/344*    (2006.01)

(52) U.S. Cl.
CPC ............. *G01N 35/02* (2013.01); *B07C 5/344* (2013.01)

(58) Field of Classification Search
CPC ............. G01N 35/02; G01N 33/48792; G01N 2035/0405; G01N 2035/0449;
(Continued)

(56) References Cited

U.S. PATENT DOCUMENTS 4,133,642 A  *  1/1979  Nosaka ............ G01N 35/00732
                                                   422/561
4,578,716 A  *  3/1986  van Rijckevorsel .........................
                                                G01N 35/00732
                                                   360/137
(Continued)

FOREIGN PATENT DOCUMENTS

DE    27 58 437        2/1984
GB    1 423 185 A      1/1976
(Continued)

OTHER PUBLICATIONS

International Preliminary Report on Patentability received in corresponding International Application No. PCT/JP2020/044721 dated Jul. 21, 2022.
(Continued)

*Primary Examiner* — Jennifer Wecker
*Assistant Examiner* — Britney N. Washington
(74) *Attorney, Agent, or Firm* — MATTINGLY & MALUR, PC

(57) ABSTRACT

Provided are a specimen transport device, a specimen analysis system, a specimen pretreatment system, and a specimen transport method that can reduce human errors as compared with the related art. There are a plurality of magnetic bodies having different inductance characteristics, and a calculation unit calculates inductance characteristic values at a predetermined current value flowing through a magnetic pole detected by a current detection unit and specifies the type of the magnetic body having different inductance characteris-
(Continued)

tics based on the obtained characteristic values to identify a holder.

9 Claims, 7 Drawing Sheets

(58) Field of Classification Search
CPC ..... G01N 35/00732; G01N 2035/0477; G01N 35/04; B07C 5/344; B65G 2201/0261; B65G 54/02
See application file for complete search history.

(56) References Cited

U.S. PATENT DOCUMENTS

| | | | |
|---|---|---|---|
| 4,780,283 A | 10/1988 | Meinecke et al. | |
| 6,017,496 A * | 1/2000 | Nova | G11C 13/0014 |
| | | | 506/40 |
| 2014/0234065 A1* | 8/2014 | Heise | B65G 54/02 |
| | | | 414/749.2 |
| 2018/0210001 A1* | 7/2018 | Reza | B01L 9/06 |
| 2021/0398723 A1* | 12/2021 | Aoyama | H02K 11/225 |
| 2022/0144556 A1* | 5/2022 | Aoyama | H02P 6/185 |

FOREIGN PATENT DOCUMENTS

| | | | |
|---|---|---|---|
| GB | 1 425 964 A | | 2/1976 |
| JP | 51-113665 A | | 10/1976 |
| JP | 59-231690 A | | 12/1984 |
| JP | 63-192472 A | | 8/1988 |
| JP | 5-153704 A | | 6/1993 |
| JP | 09-178708 A | | 7/1997 |
| JP | 10-192794 A | | 7/1998 |
| JP | 2017-77971 A | | 4/2017 |
| JP | 2018-119962 A | | 8/2018 |
| JP | 2018-165689 | | 10/2018 |
| JP | 2020-106354 A | | 7/2020 |
| WO | 2011-036190 A1 | | 3/2011 |
| WO | 2018/213400 A1 | | 11/2018 |

OTHER PUBLICATIONS

Extended European Search Report received in corresponding European Application No. 20911613.6 dated Dec. 14, 2023.
Partial Supplementary European Search Report received in corresponding European Application No. 20911316.6 dated Dec. 13, 2023.
International Search Report of PCT/JP2020/044721 dated Jan. 26, 2021.
Chinese Office Action received in corresponding Chinese Application No. 202080091383.1 dated Jun. 13, 2025.

* cited by examiner

[FIG. 1]
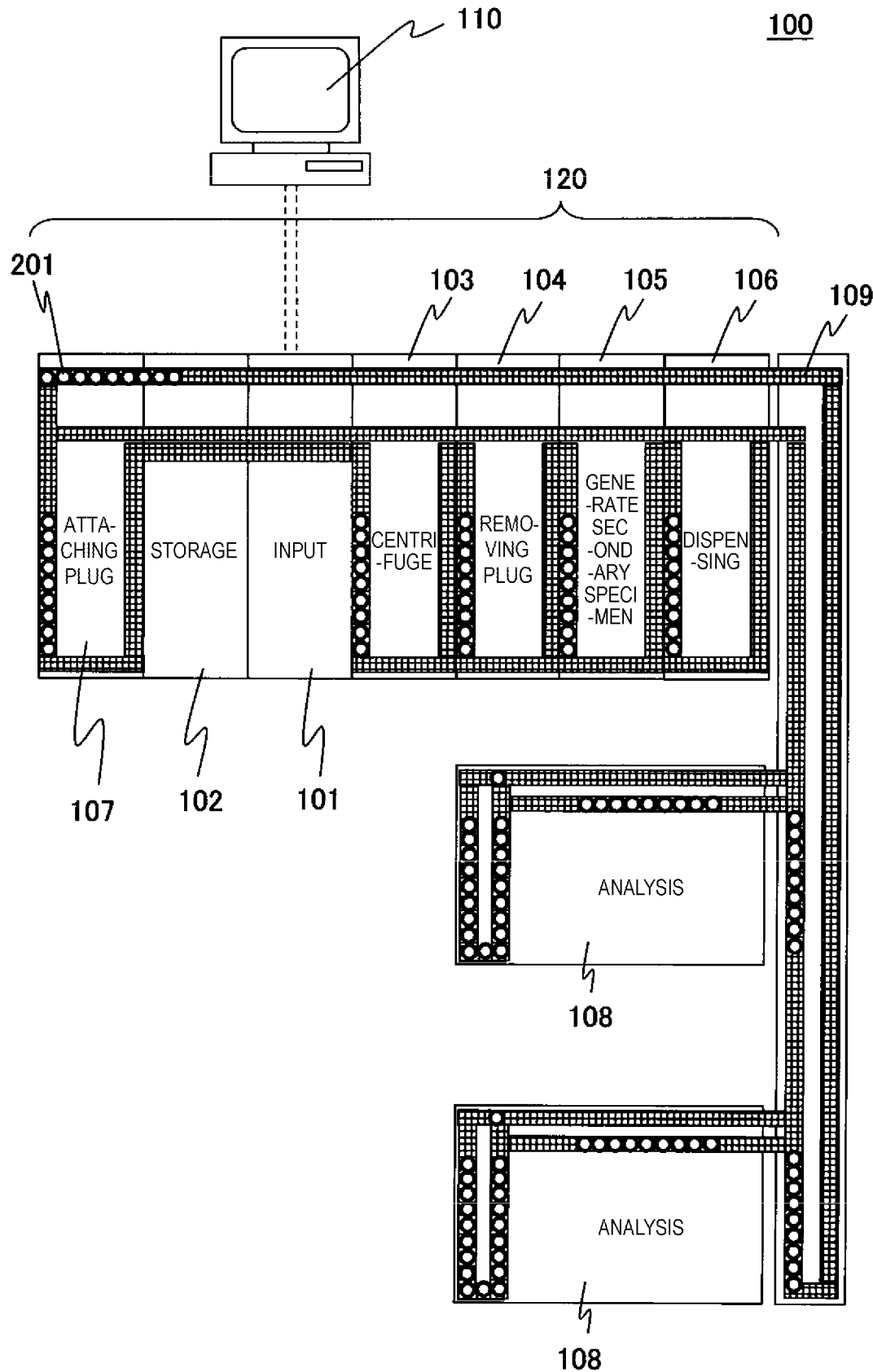

[FIG. 2]
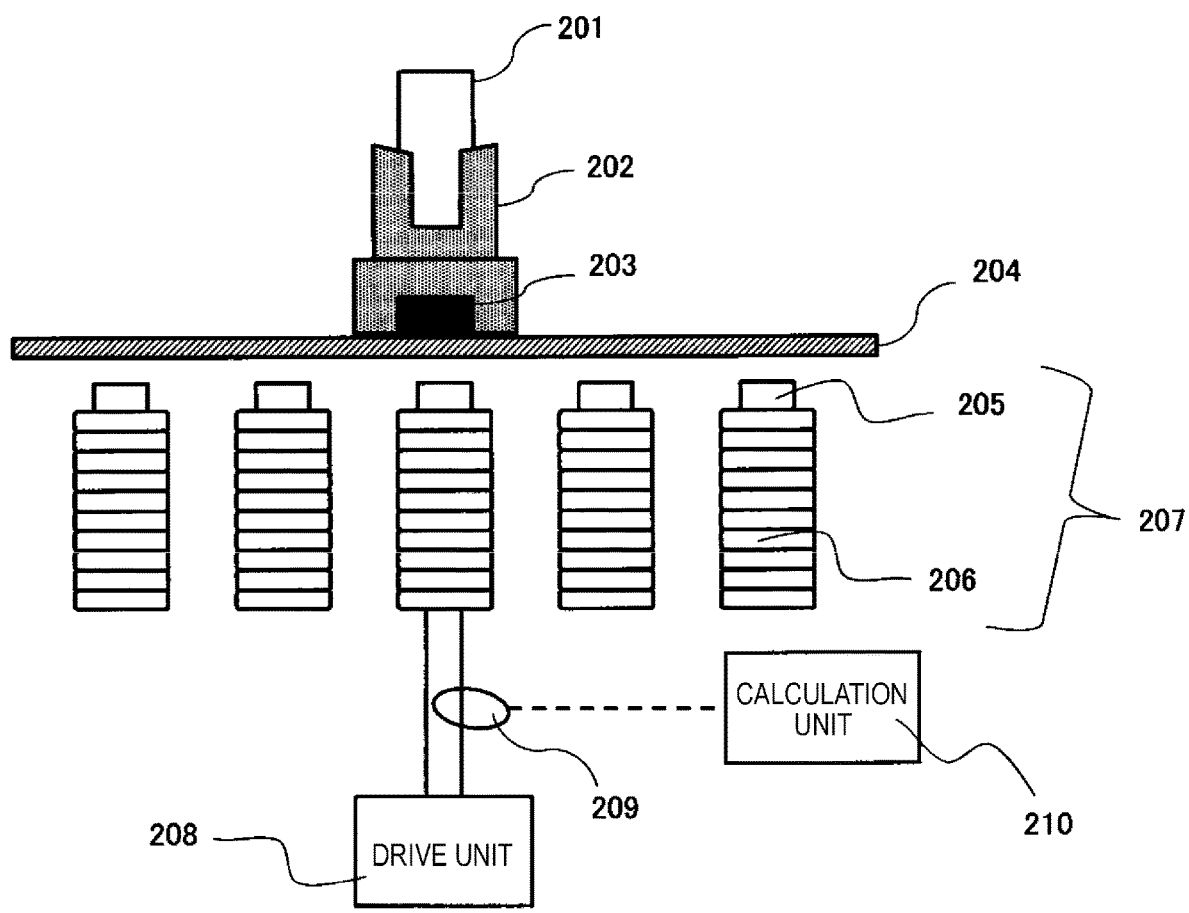

[FIG. 3]
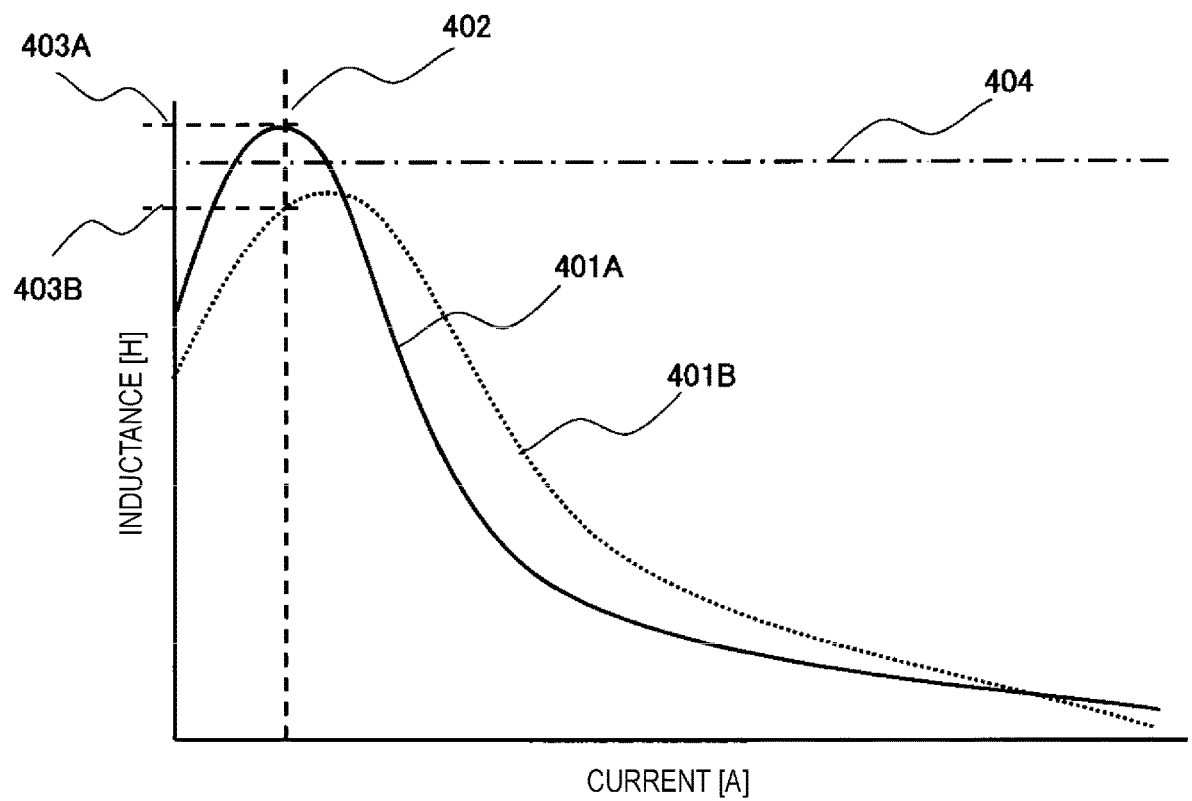

[FIG. 4]
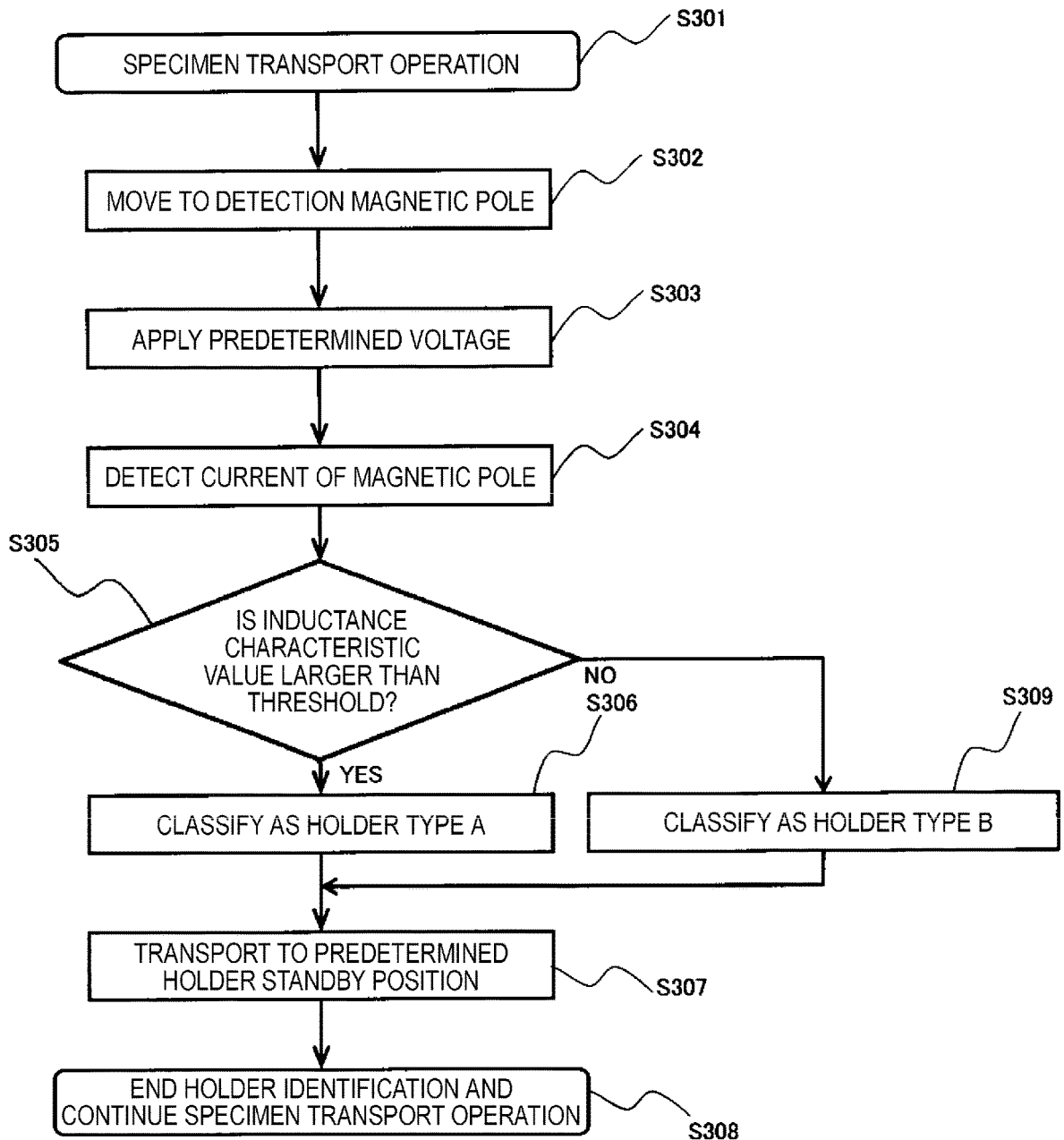

[FIG. 5]
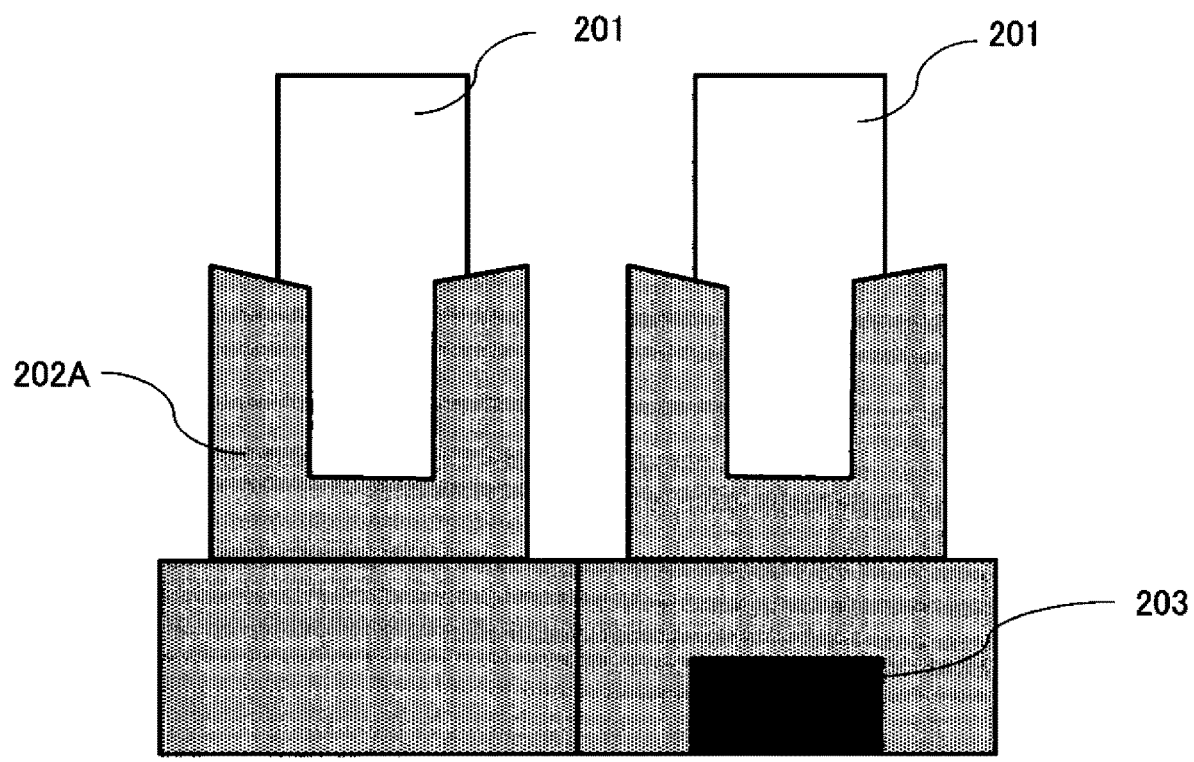

[FIG. 6]
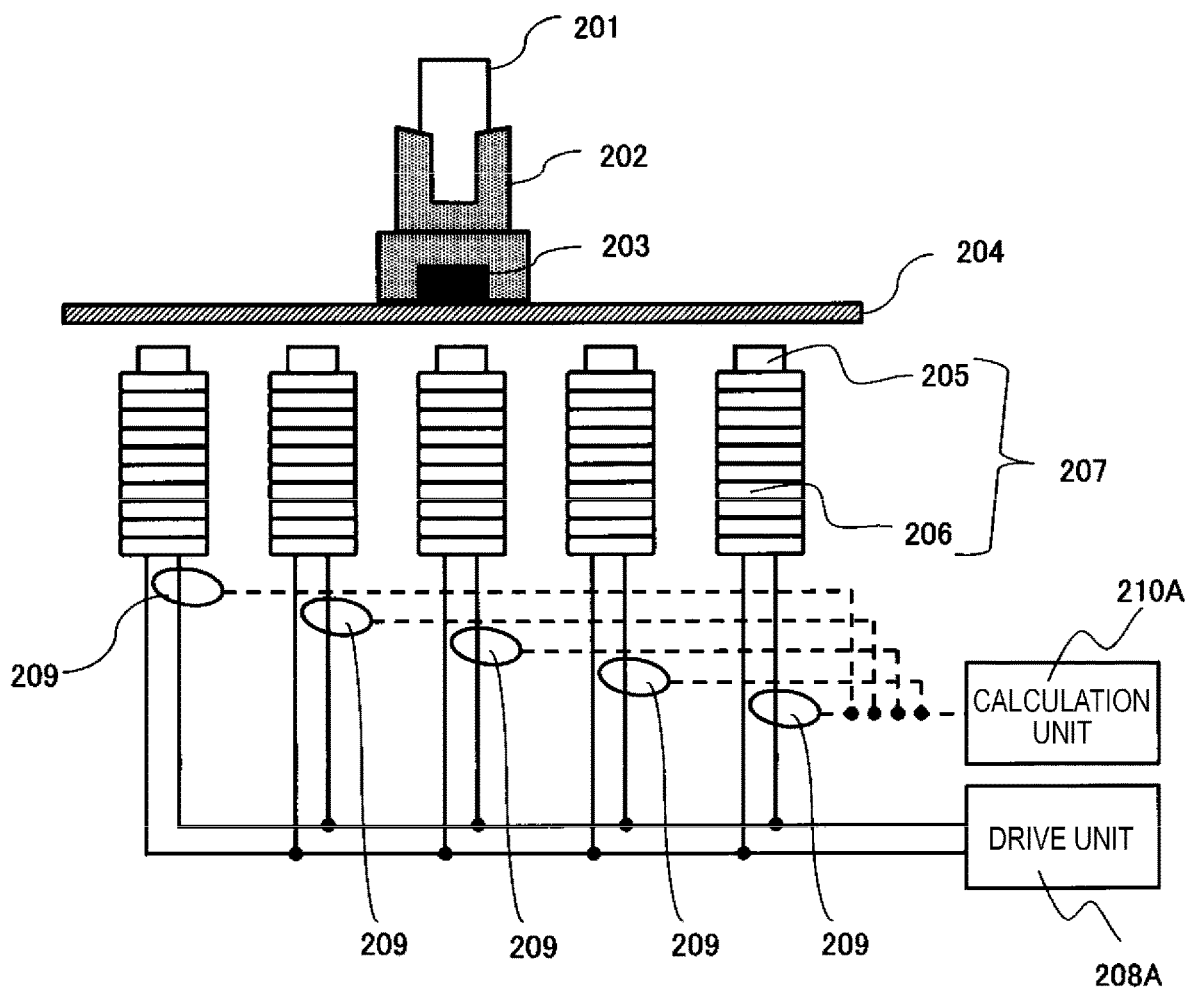

[FIG. 7]
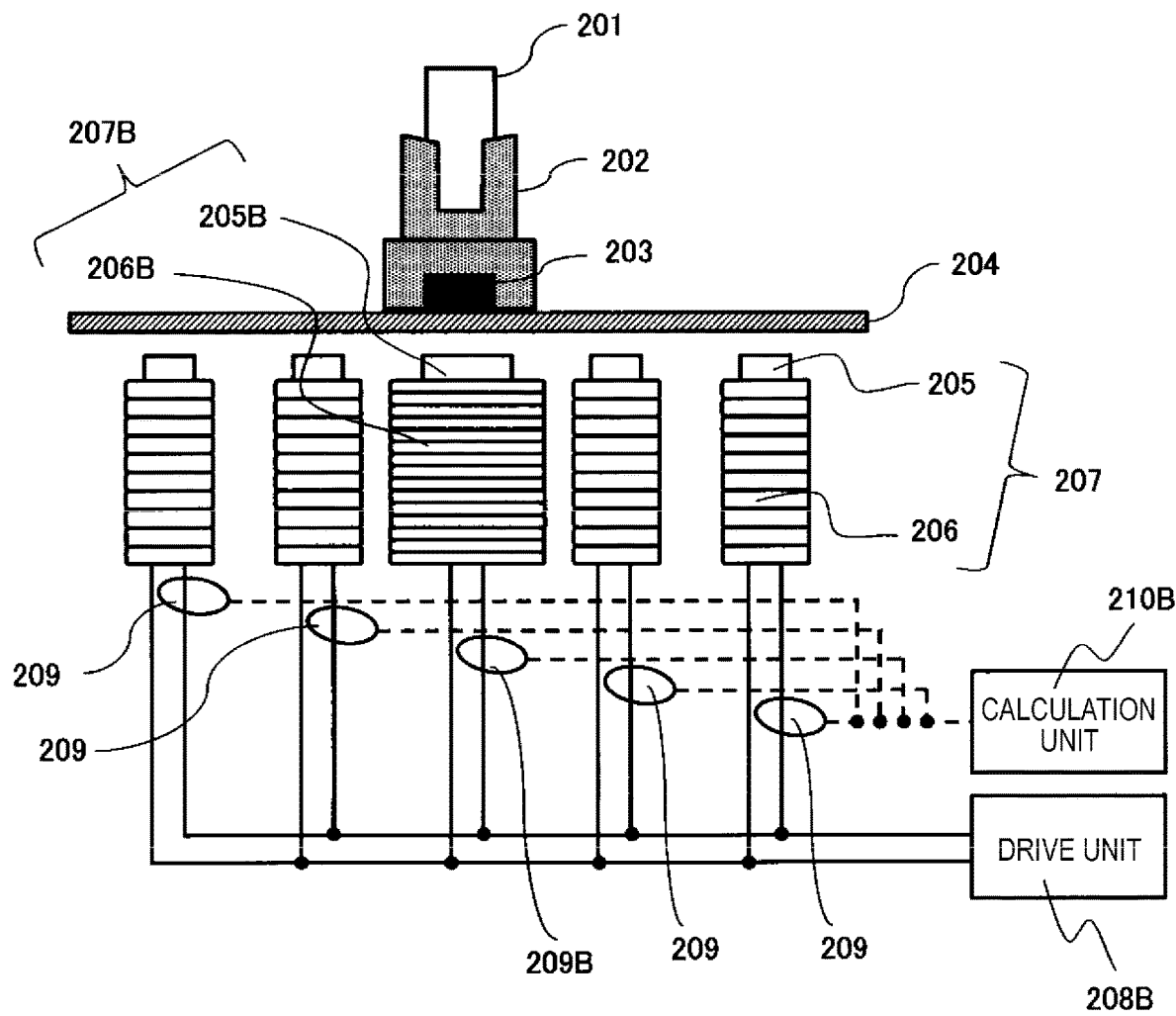

SPECIMEN TRANSPORT DEVICE, SPECIMEN ANALYSIS SYSTEM, SPECIMEN PRETREATMENT SYSTEM, AND SPECIMEN TRANSPORT METHOD

TECHNICAL FIELD

The present invention relates to a specimen transport device used in a specimen analysis system for analyzing a biological sample (hereinafter, referred to as a specimen) such as blood, plasma, serum, urine, and other body fluid or a specimen pretreatment system for performing pretreatment necessary for analysis, and a specimen transport method.

BACKGROUND ART

As an example of a laboratory sample distribution system and a corresponding method of operation that are highly-flexible and offer a high transport performance, PTL 1 discloses a laboratory sample distribution system including more than one tube carrier, each of the tube carriers including at least one magnetically active device, preferably including at least one permanent magnet, and being adapted to transporting a sample tube, a transport plane adapted to transporting the tube carriers, and more than one electromagnetic actuators stationary below the transport plane, the electromagnetic actuators being adapted to moving the tube carriers on the transport plane by applying a magnetic force to the tube carriers.

As an example of a laboratory sample distribution system in which a position on a transport surface can be recognized, PTL 2 describes a laboratory sample distribution system including a transport surface, a plurality of sample tube carriers, a drive unit configured to move the sample tube carriers on the transport surface, and a control device configured to control the movement of the sample tube carriers on the transport surface by driving the drive unit such that the sample tube carriers move along a corresponding transport path, in which a plurality of optically recognizable geometric shapes are placed on the transport surface, and each of the geometric shapes represents a dedicated field on the transport surface.

CITATION LIST

Patent Literature

PTL 1: JP-A-2017-77971
PTL 2: JP-A-2018-119962

SUMMARY OF INVENTION

Technical Problem

Examples of a specimen processing system for automatically analyzing a specimen include a specimen pretreatment system that performs input, centrifugal separation, dispensing processing, labeling processing and the like of the specimen, and a specimen analysis system that analyzes the specimen processed by the specimen pretreatment system.

In the specimen pretreatment system or the specimen analysis system, a transport line of a specimen including a belt conveyor or the like is provided to transport the specimen to a mechanism that performs predetermined processing or analysis. The specimen is transported to a predetermined mechanism by mounting a plurality of the transport lines on a specimen transport device.

In recent years, an importance of specimen processing has been increased due to sophistication of medical treatment and a progress of an aging society. Therefore, in order to improve an analysis processing capacity of the specimen analysis system, high-speed transport, simultaneous mass transport, and transport in a plurality of directions of a specimen are desired.

Examples of a technique of implementing such transport, include techniques described in PTLs 1 and 2.

Here, in a specimen transport device, various specimens such as a general specimen for performing normal processing, an emergency specimen for which rapid transport and analysis processing are required, or a control specimen for performance confirmation are transported and processed, and a user visually identifies a specimen tube according to use.

Therefore, in a transport method by an electromagnetic actuator using specimen holders described in PTLs 1 and 2, a transport operation of a plurality of specimen holders is performed in a specimen transport unit on a plane, and a human error such as misplacement of the specimen to the specimen holders may occur. Accordingly, improvement is desired.

An object of the invention is to provide a specimen transport device, a specimen analysis system, a specimen pretreatment system, and a specimen transport method capable of reducing human errors as compared with those in the related art.

Solution to Problem

The invention includes a plurality of methods for solving the above problems, and as an example thereof, there is provided a specimen transport device including: a first magnetic body provided in a transport holder in which a specimen tube storing a specimen is installed; a magnetic circuit including a second magnetic body and a winding wound around the outer periphery of the second magnetic body; a drive unit configured to supply a current to the winding of the magnetic circuit; a current detection unit configured to detect a current value flowing in the magnetic circuit; and a calculation unit configured to identify the transport holder based on a predetermined current value flowing through the magnetic circuit detected by the current detection unit, in which the first magnetic body includes a plurality of magnetic bodies having different inductance characteristics, and the calculation unit calculates an inductance characteristic value at a predetermined current value flowing through the magnetic circuit detected by the current detection unit and specifies the type of the first magnetic body having the different inductance characteristics based on the obtained inductance characteristic value to identify the transport holder.

Advantageous Effect

According to the invention, human errors can be reduced as compared with those in the related art. Problems, configurations, and effects other than those described above will be clarified with the following description of examples.

BRIEF DESCRIPTION OF DRAWINGS

FIG. 1 is a plan view showing a configuration of the entire specimen analysis system including a specimen transport device according to Example 1 of the present invention.

FIG. 2 is a configuration diagram of the specimen transport device according to Example 1.

FIG. 3 is a current superimposition characteristic graph of the inductance of a magnetic body in the specimen transport device according to Example 1.

FIG. 4 is a flowchart illustrating an operation of the specimen transport device according to Example 1 at the time of detecting a holder.

FIG. 5 is a configuration diagram of an example of a holder according to the present invention.

FIG. 6 is a configuration diagram of a transport device according to Example 2 of the present invention.

FIG. 7 is a configuration diagram of a transport device according to Example 3 of the present invention.

DESCRIPTION OF EMBODIMENTS

Hereinafter, examples of a specimen transport device, a specimen analysis system, a specimen pretreatment system, and a specimen transport method of the invention will be described with reference to the drawings.

In the following examples, it is needless to say that elements (including element steps and the like) are not necessarily essential unless otherwise particularly specified or clearly considered as essential in principle.

In all the drawings for showing the examples, the same members are denoted by the same reference numerals in principle, and the repeated description thereof is basically omitted.

Example 1

Example 1 of the specimen transport device, the specimen analysis system, the specimen pretreatment system, and the specimen transport method of the invention will be described with reference to FIGS. 1 to 5.

First, a configuration of the entire specimen analysis system including the specimen transport device will be described with reference to FIG. 1. FIG. 1 is a plan view showing the configuration of the entire specimen analysis system including the specimen transport device according to Example 1 of the invention.

In FIG. 1, a specimen analysis system 100 according to Example 1 is a system for automatically analyzing a component of a specimen such as blood or urine.

Main components of the specimen analysis system 100 include a specimen input unit 101, a specimen storage unit 102, a centrifugal processing unit 103, a plug removing processing unit 104, a secondary specimen tube generation processing unit 105, a dispensing processing unit 106, a plug attaching processing unit 107, analysis processing units 108, a specimen transport unit 109, and a control unit 110.

The specimen input unit 101 inputs a specimen tube 201 storing a specimen into the specimen analysis system 100. The specimen input unit 101 includes a specimen recognition unit, a plug detection unit, and a specimen holder recognition unit (all of which are omitted for convenience of illustration). The specimen input unit 101 recognizes a tube type of the specimen tube 201 (see FIG. 2) to be transported, a shape of a plug of a tube, and ID information assigned to a holder 202 (see FIG. 2) in which the specimen tube 201 is disposed, and obtains information for specifying the specimen tube 201 to be transported.

The specimen holder recognition unit is provided at plural positions in the specimen analysis system 100, and a location of the specimen tube 201 can be confirmed by the specimen holder recognition unit at the positions.

The centrifugal processing unit 103 performs centrifugal separation on the input specimen tube 201.

The plug removing processing unit 104 is a unit that performs a process of removing the plug from the input specimen tube 201.

The secondary specimen tube generation processing unit 105 prepares another specimen tube 201 necessary for dispensing the specimen stored in the input specimen tube 201 into the subsequent dispensing processing unit 106, and attaches a bar code or the like.

The dispensing processing unit 106 parcels out the specimen into the other specimen tube 201 prepared by the secondary specimen tube generation processing unit 105 to analyze the uncentrifuged specimen or the specimen centrifuged by the centrifugal processing unit 103 by the analysis processing units 108 or the like.

The plug attaching processing unit 107 is a unit that attaches the plug to the specimen tube 201 from which the plug was removed and the specimen tube 201 into which the specimens are parceled out. The specimen analysis system 100 may also include two or more plug attaching processing units 107 in accordance with a type of the plug used to be attached to the specimen tube 201.

The analysis processing units 108 transport the specimen processed by the processing units in the specimen analysis system 100 and perform qualitative and quantitative analysis of a component of the specimen. Analysis items in the units are not particularly limited, and a configuration of a known automatic analysis device for analyzing biochemical items and immune items may be employed. Further, when a plurality of analysis processing units are provided, the analysis processing units may have the same or different specifications, and are not particularly limited.

The specimen storage unit 102 is a unit that stores the specimen tube 201 from which the plug has been removed by the plug attaching processing unit 107.

The specimen transport unit 109 transports the specimen tube 201 input from the specimen input unit 101 or the specimen tube 201 in which the specimen is dispensed by the dispensing processing unit 106 and parceled out to units in the specimen analysis system 100 such as the centrifugal processing unit 103, the dispensing processing unit 106, and the analysis processing units 108. The specimen transport unit 109 is also used for transport to mechanisms that perform a predetermined operation in units such as the centrifugal processing unit 103, the dispensing processing unit 106, and the analysis processing unit 108.

Accordingly, the holder 202 in which the specimen tube 201 input from the specimen input unit 101 is installed is transported to a predetermined pretreatment unit via the specimen transport unit 109, and then transported to the analysis processing units 108.

The control unit 110 controls the operation of units in the specimen analysis system 100 and mechanisms in the units and analyzes measurement data in the analysis processing units 108, and is implemented by a computer including a display device such as a liquid crystal display, an input device, a storage device, a CPU, a memory, and the like. The control unit 110 can confirm the location of the specimen in the specimen analysis system 100 from the ID information of the holder 202 by communicating with the units and the mechanisms described above.

Control of the operation of devices by the control unit 110 is executed based on various programs recorded in the storage device in the control unit 110.

Operation control processing executed by the control unit 110 may be integrated into one program, may be divided into a plurality of programs, or may be performed in a combination thereof. Further, a part or all of the programs may be implemented by a dedicated hardware, or may be modularized.

In FIG. 1, the specimen transport unit 109 is implemented by a combination of a plurality of specimen transport devices of the invention described later. Alternatively, the specimen transport device of the invention may be implemented by the specimen transport device described later, or a combination of a specimen transport device not including a calculation unit 210 described later and the specimen transport device described later. The specimen transport unit 109 may include at least one or more specimen transport devices of the invention.

In FIG. 1, the specimen analysis system 100 includes various types of pretreatment units such as the specimen input unit 101 for specimen pretreatment. Alternatively, the specimen analysis system may be used as a system (a system in which the plurality of analysis processing units 108 are connected by the specimen transport device) not including the units for pretreatment.

The invention can also be applied to a transport device that connects units in a specimen pretreatment system in which the analysis processing units 108 are omitted from the specimen analysis system 100.

Next, a configuration of the specimen transport device according to Example 1 of the invention will be described with reference to FIG. 2. FIG. 2 is a configuration diagram of the specimen transport device according to Example 1 of the invention.

In FIG. 2, a plurality of holders 202 in each of which the specimen tube 201 storing the specimen is installed are provided in the specimen transport device. Magnetic bodies 203 having different inductance characteristics depending on a difference in at least one of the material, the density, and the shape are provided on a bottom surface portion of each of the plurality of holders 202.

The magnetic body 203 is implemented by a permanent magnet such as neodymium and ferrite, and may also be implemented by other magnets and soft magnetic bodies, and the materials can be appropriately combined.

It is not necessary that all the inductance characteristics of the magnetic bodies 203 of the holders 202 in the specimen transport device are different, as long as the inductance characteristics are divided into at least two types of ranges including a group of inductance characteristics according to specifications within a specific range and a group of inductance characteristics according to specifications within a specific range distinctly different from the range in the other group.

It is not necessary to provide the magnetic body 203 on a lower surface of the holder 202, and it is desirable to provide the magnetic body 203 on the lower surface from a viewpoint of a range over which a transport force of electromagnetic transport is exerted.

The holder 202 including the magnetic body 203 slides on a transport surface 204. In order to generate the transport force, a plurality of magnetic poles 207 each including a columnar core 205 and a winding 206 wound around an outer periphery of the core 205 are provided below the transport surface 204.

The magnetic pole 207 is connected to a drive unit 208 that applies a predetermined voltage to the magnetic pole 207 to flow a predetermined current through the winding 206. In the present example, the drive unit 208 is similarly connected to the other magnetic poles 207, which is omitted for convenience of illustration.

The magnetic pole 207 to which the voltage is applied by the drive unit 208 serves as an electromagnet, and attracts the magnetic body 203 in the holder 202 on the transport surface 204. After the holder 202 is attracted by the magnetic pole 207, voltage application from the drive unit 208 to the magnetic pole 207 is stopped, and the magnetic body 203 in the holder 202 is attracted to the adjacent magnetic pole by applying the voltage from the drive unit 208 to a different magnetic pole adjacent to the magnetic pole 207 in the same manner as described above.

By repeating this procedure on all the adjacent magnetic poles 207, the holder 202 moves on the transport surface 204, that is, the specimen stored in the specimen tube 201 held in the holder 202 provided with the magnetic body 203 is transported to a destination.

The current flowing through the winding 206 of the magnetic pole 207 during transport is detected by a current detection unit 209. The current detection unit 209 executes a current detection step of detecting a current value flowing when the current is supplied to the winding 206 of the magnetic pole 207. The current flowing through the winding 206 of the magnetic pole 207 detected by the current detection unit 209 is transmitted to the calculation unit 210 to be digitized.

In the present example, it is desirable that the current detection unit 209 detects the current value when each of the different holders 202 is in the same region, more preferably when each of the different holders 202 is stopped in the same region. However, the current value may be detected during transport. Even during the transport, it is desirable to detect the current value when each of the different holders 202 is in the same region.

As a unit for specifying the holders existing in the same range, a known unit such as a Hall element or various units can be used.

The calculation unit 210 calculates the current flowing through each winding 206 using various pieces of information such as position information, speed information, and weight information on the holder 202, and outputs a command signal to the corresponding drive unit 208. The drive unit 208 applies a voltage to the corresponding winding 206 based on the command signal.

In addition, the calculation unit 210 of the present example identifies the holder 202 based on a predetermined current value flowing through the magnetic pole 207 detected by the current detection unit 209. More specifically, the holder 202 is identified by calculating inductance characteristic values 403A and 403B (see FIG. 3) at the predetermined current value flowing through the magnetic pole 207 detected by the current detection unit 209 and specifying a type of the magnetic body 203 having different inductance characteristics depending on the obtained inductance characteristic values 403A and 403B. That is, a calculation step is executed by the calculation unit 210.

Hereinafter, a current superimposition characteristic of an inductance of the magnetic body 203 of the holder 202 according to the invention will be described with reference to FIG. 3. FIG. 3 is a graph showing the current superimposition characteristic of the inductance of the magnetic body 203 according to the present example.

The current superimposition characteristic is a characteristic that the inductance characteristic value decreases as the magnetic body approaches magnetic saturation when a direct current flows, and the inductance characteristic value decreases by increasing the flowing current.

The magnetic body 203 in the holder 202 has an inductance waveform 401A or an inductance waveform 401B indicating a specific current superimposition characteristic as shown in FIG. 3 depending on the material, the shape, and the like. The inductance characteristic value 403A, which is a value of the inductance waveform 401A at a specific current value 402, and the inductance characteristic value 403B, which is a value of the inductance waveform 401B, are stored in the calculation unit 210.

By setting a predetermined threshold 404 to a range in which the inductance characteristic values 403A and 403B can be identified from each other, a difference between the magnetic bodies 203 can be identified, and the holders 202 can be identified into a holder type A and a holder type B. By this method, a type of the holder 202 (for general specimen, emergency specimen, standard sample, accuracy control sample, or the like) is identified, or the type of the specimen tube 201 (general specimen, emergency specimen, standard sample, accuracy control sample, or the like) installed in the holder 202 is identified.

The calculation unit 210 can be implemented by controlling a computer including a CPU, a memory, an interface, and the like or a field-programmable gate array (FPGA) to read programs and execute the calculation. These programs are stored in an internal recording medium or an external recording medium (not shown) in each of the configurations, and are read and executed by the CPU.

The operation control processing may be integrated into one program, may be divided into a plurality of programs, or may be a combination thereof. Further, a part or all of the programs may be implemented by dedicated hardware, or may be modularized. Further, the various programs may be installed in a corresponding device from a program distribution server, the internal recording medium, or the external recording medium.

Further, the programs are not necessary to be independent of the drive unit 208 and the like, and two or more may be integrated and shared, and only the processing may be shared. In addition, at least a part of the configuration may be connected via a wired or wireless network.

Next, a holder detection operation of the specimen transport device when the specimen according to the present example is transported will be described with reference to FIG. 4. FIG. 4 is a flowchart showing an operation of the transport device according to Example 1 of the invention when detecting the holder.

As shown in FIG. 4, first, the transport of the holder 202 holding the specimen tube 201 storing the specimen is started by the specimen transport unit 109 of the specimen analysis system 100 (step S301).

During the specimen transport operation, the holder 202 is transported to the magnetic pole 207 that detects the current flowing through the winding 206 by the current detection unit 209 shown in FIG. 2 (step S302).

After the holder 202 is transported to above the predetermined magnetic pole 207, the predetermined voltage is applied to the magnetic pole 207 from the drive unit 208 (step S303).

The current value flowing through the winding 206 of the magnetic pole 207 due to the predetermined voltage applied in step S303 is detected by the current detection unit 209 and transmitted to the calculation unit 210 (step S304).

In the storage device of the calculation unit 210, a relationship between the current value flowing through the winding 206 of the magnetic pole 207 and the inductance characteristic value of the magnetic body 203 of the holder 202 corresponding to the current value is recorded in advance, and the inductance characteristic value of the magnetic body 203 of the holder 202 transported to above the magnetic pole 207 is detected based on the current value detected by the current detection unit 209 (step S305).

In addition, the calculation unit 210 determines whether the inductance characteristic value of the holder 202 including the magnetic body 203 exceeds the predetermined threshold based on the current value detected in step S304 (step S305).

When it is determined in step S305 that the inductance characteristic value of the holder 202 exceeds the threshold, the holder 202 is classified into the "holder type A" (step S306). The holder 202 identified into the holder type A is transported to a predetermined holder standby position for the holder type A (step S307).

On the other hand, when the calculation unit 210 determines in step S305 that the inductance characteristic value of the holder 202 does not exceed the predetermined threshold, the holder 202 is identified into the "holder type B" (step S309). The holder 202 identified into the holder type B is transported to a predetermined holder standby position for the holder type B (step S307).

The identification of the holder 202 is completed by moving the holder 202 to the holder standby position for the holder type A or moving the holder 202 to the holder standby position for the holder type B. An operator installs the specimen tube 201 on the holder 202 and the normal transport operation is continued (step S308).

In FIGS. 3 and 4, the magnetic body 203 has two types of inductance characteristic values including the type A and the type B. Alternatively, even when the holder types include three or more types, it is possible to operate the three or more types of holders in the specimen transport device by repeating the processing of determining the holder in the same manner.

In this case, a plurality of thresholds for the inductance characteristic value corresponding to the magnetic body 203 in the holder 202 are stored in the calculation unit 210, and in step S305 of FIG. 4, the holders 202 are identified into a plurality of holder types by performing determination regarding the plurality of thresholds.

By repeating the processing shown in FIG. 4, the holder 202 identified by the inductance characteristic value stands by while being identified at a predetermined position. Accordingly, for example, when the operator installs the specimen tube 201 of the general specimen in the holder 202, the holder 202 for the general specimen identified into the holder type A, the holder type B, or the like is transported from the predetermined standby position to the position where the specimen tube 201 storing the general specimen is installed in the holder 202, so that it is possible to avoid the operator from erroneously installing the specimen tube 201 of the general specimen in a holder different from the holder 202 for the general specimen, as compared with that in the related art.

Similarly, by identifying the holder 202, for example, when the emergency specimen requiring rapid transport and analysis processing is transported, it is also possible to transport the emergency specimen on a transport path dedicated to the holder 202 for the emergency specimen, which is different from the holder 202 for the general specimen and is also provided on the specimen transport unit 109, and a more rapid transport operation can be performed.

Next, a structure of the holder 202 will be described. FIG. 5 is a configuration diagram of an example of the holder according to the invention.

In the invention, since the holder type is determined based on the inductance characteristic value of the magnetic body 203 such as the permanent magnet in the holder 202, the structure of the holder 202 itself is not necessarily limited to the structure in which one specimen tube 201 is installed, and may be a structure in which a plurality of specimen tubes 201 can be installed.

For example, a holder as shown in FIG. 2 in which one specimen tube 201 is installed or a holder 202A as shown in FIG. 5 that includes two or more connected holders 202 in FIG. 2 may be used.

According to the structure of the holder 202A, two or more specimen tubes 201 can be installed with the same holder information in a measurement requiring a large number of specimens in a large number of analysis items and the like. Accordingly, compared to a case in the related art where the specimen tubes 201 are installed in separate holders 202 and operated individually, it is possible to reduce an operation of matching information of the separate holders 202 in the related art with information of the specimen tubes 201, and it is possible to reduce malfunctions such as specimen loss and specimen mistaking as compared with that in the related art.

In addition to the holders 202 and 202A holding one specimen tube 201 or two specimen tubes 201, a specimen rack holding three or more specimen tubes 201 may be used.

Next, an effect of the present example will be described.

The specimen transport device according to Example 1 of the invention described above includes the magnetic body 203 provided in the holder 202 in which the specimen tube 201 storing the specimen is installed, the magnetic pole 207 including the core 205 and the winding 206 wound around the outer periphery of the core 205, the drive unit 208 configured to supply a current to the winding 206 of the magnetic pole 207, the current detection unit 209 configured to detect the current value flowing through the magnetic pole 207, and the calculation unit 210 configured to identify the holder 202 based on the predetermined current value flowing through the magnetic pole 207 detected by the current detection unit 209. The magnetic body 203 includes a plurality of magnetic bodies having different inductance characteristics, and the calculation unit 210 calculates the inductance characteristic values 403A and 403B at the predetermined current value flowing through the magnetic pole 207 detected by the current detection unit 209 and specifies the type of the magnetic body 203 having the different inductance characteristics based on the obtained inductance characteristic values 403A and 403B to identify the holder 202.

Accordingly, in a transport method by an electromagnetic actuator, it is possible to determine the type of the holder 202 in which the specimen tube 201 is installed by using the magnetic body 203 on the holder 202 that is necessary for transport, and it is possible to increase a material for determining the type as compared with that in the related art. Therefore, as the device and the specimen transport device, the specimen holder type can be automatically determined with higher accuracy, and the identification work by a user can be reduced or eliminated. Therefore, since the holder 202 can be prevented from being transported to a wrong position, effects of further improving work efficiency of the user and further reducing human errors can be obtained.

In particular, although one holder can achieve more flexible transport corresponding to operating conditions than five racks do, according to the invention, it can be said that the effect of reducing errors is improved as compared with that in the related art since methods for determining the type of the holder 202 are increased and the type of the holder 202 can be identified with higher accuracy than that in the related art.

Further, from an actual operation aspect of the specimen pretreatment system 120 or the specimen analysis system 100, when the specimen transport device capable of identifying the type of the holder 202 described above is disposed immediately before a buffer or the specimen storage unit 102 in which an empty holder after the processing by the specimen pretreatment system 120 and analysis by the specimen analysis system 100 remains, the effect of identifying the holder types with higher accuracy can be further received.

In addition, since the magnetic body 203 has different inductance characteristics depending on the difference in at least one of the material, the density, and the shape, the inductance characteristics can be easily changed on the magnetic body 203, and accuracy of identifying the holder 202 can be achieved with a simpler configuration.

Further, since the current detection unit 209 detects the current value when each of the different holders 202 is in the same region, in particular, detects the current value when each of the different holders 202 is stopped in the same region, accuracy of obtaining the inductance characteristic values 403A and 403B can be improved, the type of the holder 202 can be more accurately identified.

Example 2

A specimen transport device, a specimen analysis system, a specimen pretreatment system, and a specimen transport method according to Example 2 of the invention will be described with reference to FIG. 6. FIG. 6 is a configuration diagram of the specimen transport device according to Example 2 of the invention.

The specimen transport device of the present example shown in FIG. 6 includes the plurality of magnetic poles 207, a drive unit 208A configured to individually apply a voltage to each of the plurality of magnetic poles 207, a plurality of current detection units 209 configured to detect the current values flowing through the windings 206 of the magnetic poles 207 due to the voltage applied by the drive unit 208A, and a calculation unit 210A configured to identify types of the holders 202 in the magnetic poles 207 based on the current values detected by the plurality of current detection units 209.

Other configurations and operations are substantially the same as the configurations and operations of the specimen transport device, the specimen analysis system, and the specimen pretreatment system and the specimen transport method of Example 1 described above, and details are omitted.

Also in the specimen transport device, the specimen analysis system, the specimen pretreatment system, and the specimen transport method according to Example 2 of the invention, the effects substantially the same as those of the specimen transport device, the specimen analysis system, and the specimen pretreatment system and the specimen transport method of Example 1 described above can be obtained.

In addition, since there are a plurality of locations where inductance characteristic values of the holders 202 are obtained by including the plurality of magnetic poles 207, the plurality of current detection units 209, at least one or more drive units 208, and at least one or more calculation units 210, timings at which the types of the holders 202 are identified can be increased, and a structure in which a transport error is less likely to occur can be obtained.

In addition, since the structures of the magnetic poles 207 and the drive unit 208 necessary for the normal specimen transport operation are the same as those of Example 1, the holder 202 can be identified with higher accuracy even during the transport operation of the holder 202. Therefore, for example, even in the holder 202 in the transport operation in which the predetermined transport operation is completed and the holder 202 is returned to a predetermined holder standby position or a position where the specimen tube 201 is additionally installed, the holder 202 can be identified during the transport operation of returning, which can contribute to shortening time for preparing transport operation.

In the present example, the calculation unit 210A and the drive unit 208A may be plural.

Example 3

A specimen transport device, a specimen analysis system, a specimen pretreatment system, and a specimen transport method according to Example 3 of the invention will be described with reference to FIG. 7. FIG. 7 is a configuration diagram of the specimen transport device according to Example 3 of the invention.

In the specimen transport device of the present example shown in FIG. 7, a specific magnetic pole 207B of the specimen transport device of Example 2 is a circuit in which shapes of a core 205B and a winding 206B are different from those of the cores 205 and the windings 206 of the other magnetic poles 207. At least one or more magnetic poles 207B may be provided in the specimen transport device, and the number thereof is not particularly limited.

The shape of either the core 205B or the winding 206B of the specific magnetic pole 207B may be different from those of the cores 205 and the windings 206 of the other magnetic poles 207. In addition, not only the shape but also one or more of the material, the density, and the shape may be different from those of the cores 205 and the windings 206 of the other magnetic poles 207.

In the calculation unit 210B of the present example, a threshold of an inductance characteristic value is set for each of the adjacent magnetic poles 207 having different configurations. Then, the different inductance characteristics of the magnetic bodies 203 are calculated based on detection values from a current detection unit 209B that detects the current flowing through the specific magnetic pole 207B and the current detection units 209 that detect the current flowing through the other magnetic poles 207. Accordingly, during the normal transport operation of the holders 202, the inductance characteristic values detected when the holders 202 pass above the magnetic poles 207 and 207B are compared between the adjacent magnetic poles 207 and 207B.

A configuration of a drive unit 208B that applies a voltage to the specific magnetic pole 207B and the other magnetic poles 207 is the same as that of the drive unit 208A of Example 2.

The other configurations and operations are substantially the same as the configurations and operations of the specimen transport device, the specimen analysis system, and the specimen pretreatment system and the specimen transport method of Example 1 described above, and details are omitted.

Also in the specimen transport device, the specimen analysis system, the specimen pretreatment system, and the specimen transport method according to Example 3 of the invention, the effects substantially the same as those of the specimen transport device, the specimen analysis system, the specimen pretreatment system and the specimen transport method of Example 1 described above can be obtained.

The magnetic pole 207B has a circuit in which one or more of the material, the density, and the shape of at least one of the cores 205, 205B and the windings 206, 206B are different, and the calculation unit 210B can identify the holder type in a more detailed range by calculating the different inductance characteristics of the magnetic body 203 detected by the magnetic poles 207 and 207B having different configurations. It is possible to provide a position where only a specific holder identification that is not related to the transport operation is performed, and the position can be used when an operator manually identifies the holder 202 in normal use and installs the specimen tube 201.

Similarly to the configurations shown in FIGS. 2 and 6, it is needless to say that the different magnetic pole 207B shown in FIG. 7 can also be used as the magnetic pole used for the normal transport operation.

<Others>

The invention is not limited to the above examples, and includes various modifications. The examples described above have been described in detail for easy understanding of the invention, and are not necessarily limited to those including all the configurations described above.

Further, a part of a configuration of one example can be replaced with a configuration of another example, and the configuration of the other example can be added to the configuration of the one example. A part of a configuration of each example may be added or replaced with another configuration, and one configuration may be deleted from the part of the configuration.

REFERENCE SIGN LIST

100: specimen analysis system
101: specimen input unit
102: specimen storage unit
103: centrifugal processing unit
104: plug removing processing unit
105: child specimen vessel generation processing unit
106: dispensing processing unit
107: plug attaching processing unit
108: analysis processing unit
109: specimen transport unit
110: control unit
120: specimen pretreatment system
201: specimen vessel
202, 202A: holder (transport container)
203: magnetic body (first magnetic body)
204: transport surface
205, 205B: core (second magnetic body)
206, 206B: winding
207, 207B: magnetic pole (magnetic circuit)
208, 208A, 208B: drive unit
209, 209B: current detection unit
210, 210A, 210B: calculation unit
401A, 401B: inductance waveform
402: current value
403A, 403B: inductance characteristic value
404: threshold

The invention claimed is:

1. A specimen transport device comprising:
a first magnetic body provided in a transport container in which a specimen vessel storing a specimen is installed;

a magnetic circuit including a second magnetic body and a winding wound around the outer periphery of the second magnetic body;

a drive unit configured to supply a current to the winding of the magnetic circuit;

a current detection unit configured to detect a current value flowing in the magnetic circuit; and a calculation unit configured to identify the transport container based on a predetermined current value flowing through the magnetic circuit detected by the current detection unit, wherein the first magnetic body includes a plurality of magnetic bodies having different inductance characteristics, and the calculation unit calculates an inductance characteristic value at a predetermined current value flowing through the magnetic circuit detected by the current detection unit and specifies the type of the first magnetic body having the different inductance characteristics based on the obtained inductance characteristic value to identify the transport container.

2. The specimen transport device according to claim 1, wherein the first magnetic body has a different inductance characteristic due to a difference in at least one of material, density, and shape.

3. The specimen transport device according to claim 1, wherein a plurality of the magnetic circuits, a plurality of the current detection units, at least one or more of the drive units, and at least one or more of the calculation units are provided.

4. The specimen transport device according to claim 1, wherein the magnetic circuit has a circuit having a configuration in which at least one of the material, density, and shape of at least one of the second magnetic body and the winding is different, and the calculation unit calculates each of the different inductance characteristics of the first magnetic body detected by the magnetic circuit having a different configuration.

5. The specimen transport device according to claim 1, wherein the current detection unit detects the current value when each of the different transport containers is present in the same area.

6. The specimen transport device according to claim 5, wherein the current detection unit detects the current value when each of the different transport containers is stopped in the same area.

7. A specimen analysis system comprising the specimen transport device according to claim 1.

8. A specimen pretreatment system comprising the specimen transport device according to claim 1.

9. A method for transporting a specimen stored in a specimen vessel held by a transport container provided with a first magnetic body, wherein the first magnetic body includes a plurality of magnetic bodies having different inductance characteristics, the method comprising:

a current detection step of detecting a current value flowing when a current is supplied to a second magnetic body and a winding of a magnetic circuit having the winding wound around the outer periphery of the second magnetic body; and a calculation step of calculating an inductance characteristic value at a predetermined current value flowing through the magnetic circuit detected in the current detection step and specifying the type of the first magnetic body having the different inductance characteristics based on the obtained inductance characteristic value to identify the type of the transport container.

* * * * *